United States Patent [19]

Padilla et al.

[11] Patent Number: 6,114,285
[45] Date of Patent: Sep. 5, 2000

[54] COMPOSITIONS AND METHODS FOR USE IN CROPPING BANANAS AND PLANTAIN TREES

[75] Inventors: Marvin Donaldo Mora Padilla, San Pedro Sula, Honduras; Juan Bocanegra; Jorge Cepeda, both of Miami, Fla.

[73] Assignee: Rhone Poulenc Agro, Lyon Cedex, France

[21] Appl. No.: 09/252,029

[22] Filed: Feb. 18, 1999

Related U.S. Application Data

[60] Provisional application No. 60/075,421, Feb. 20, 1998, and provisional application No. 60/109,588, Nov. 23, 1998.

[30] Foreign Application Priority Data

Jan. 18, 1999 [GB] United Kingdom ............... 9901061

[51] Int. Cl.⁷ .......................... A01N 57/18; A01N 47/10
[52] U.S. Cl. .................... 504/184; 504/207; 504/208; 514/140; 514/477
[58] Field of Search .................... 514/560, 140, 514/477; 504/184, 208, 207

[56] References Cited

U.S. PATENT DOCUMENTS

| | | | |
|---|---|---|---|
| 5,232,940 | 8/1993 | Hatton et al. | 514/407 |
| 5,236,938 | 8/1993 | Huang et al. | 514/341 |
| 5,929,121 | 7/1999 | Cepeda et al. | 514/640 |

FOREIGN PATENT DOCUMENTS

| | | |
|---|---|---|
| 0295117 | 12/1988 | European Pat. Off. . |
| 0385809 | 9/1990 | European Pat. Off. . |
| 0403300 | 12/1990 | European Pat. Off. . |
| 0679650 | 11/1995 | European Pat. Off. . |
| 19511269 | 10/1995 | Germany . |
| 2304575 | 3/1997 | United Kingdom . |
| 2304708 | 3/1997 | United Kingdom . |
| 87/03781 | 7/1987 | WIPO . |
| 93/06089 | 4/1993 | WIPO . |
| 94/21606 | 9/1994 | WIPO . |

OTHER PUBLICATIONS

*Handbook of Chemistry and Physics*, 56$^{th}$ edition, CRC Press, Cleveland, Ohio, p. B-4 (1975).
*The Pesticide Manual*, tenth edition, Clive Tomlin, editor, British Crop Protection Council, pp. 147-148, 404-405 (1994).
*The Pesticide Manual*, eleventh edition, Clive Tomlin, editor, British Crop Protection Council, pp. 477-478, 629-630 (1997).

*Primary Examiner*—Jose' G. Dees
*Assistant Examiner*—Alton Pryor
*Attorney, Agent, or Firm*—Finnegan, Henderson, Farabow, Garrett & Dunner, L.L.P.

[57] ABSTRACT

A method of chemically suckering trees of the families Musaceae (banana) and Plantaginaceae (plantains) which comprises introducing into a mother tree an amount of a composition effective to arrest apical dominance in the mother tree.

A method of protection of two or more trees of the families Musaceae (banana) and Plantaginaceae (plantains) which share a common root system.

21 Claims, No Drawings

COMPOSITIONS AND METHODS FOR USE IN CROPPING BANANAS AND PLANTAIN TREES

CROSS-REFERENCE TO RELATED APPLICATIONS

This application claims the priority of U.S. Provisional Patent Applications No. 60/075,421, filed Feb. 20, 1998 and Ser. No. 60/109,588, filed Nov. 23, 1998, both of which are incorporated by reference herein in their entireties and relied upon.

CROSS-REFERENCE TO PRIORITY APPLICATION

This application claims priority under 35 U.S.C. § 119 of United Kingdom Patent Application No. 9901061.3, filed Jan. 18, 1999, incorporated by reference herein in its entirety and relied upon.

BACKGROUND OF THE INVENTION

1. Field of the Invention

The present invention relates to compositions and methods for cropping banana and plantain fruit.

2. Background Art

Global regulatory requirements are becoming more and more demanding with respect to the use of pesticides, particularly with respect to unmanaged or unnecessary pesticide residues. Thus there exist mutually contradictory requirements of farmers in that the need to control destructive pests very thoroughly demands that more pesticide be used, while increasing pressures from regulatory agencies demand that less pesticide be used. These regulatory demands are aimed to protect the safety and health of agricultural workers and the general public. It is also well-known that the general public would like less chemical residue on fruits and vegetables.

A particular consequence of this situation is that there is an increasing need to have more efficient methods of protection of banana trees and plantain trees. It is well-known that such fruit-producing trees attract a large number of pests, particularly destructive insects and nematodes.

A common technique for cultivating banana trees or plantain trees is by growing them on large blocks or plantations. The trees are disposed as mother plants having a series (for example 1 to 5, generally 1 to 3) of followers or peeps, that is, daughter plants, growing from the corm (that is, the base of the pseudostem) of the mother plant. In this respect, the mother and daughter plants share a common root system. At an appropriate time before the harvest of the fruit of the mother plants or trees, all the daughter plants are removed except one per mother plant which is deemed by the grower to have the best chance of survival. Such a practice allows the next generation of banana or plantain plants to be readily produced. The removal of the daughter plants is possible after the harvest of the mother plants, but it is agronomically preferred to remove them beforehand.

The fruits of the banana trees are harvested by cutting off the bunches of fruit. Afterwards, the mother trees are cut to remove the canopies. The pseudotrunks which are left are generally in a height range from 0.5 meter to 2.5 meters. Such a practice facilitates the growth of the daughter plants. The mother pseudotrunk is then left to decay or is cut down in stages until only a daughter pseudotrunk remains.

British Patent Publications GB 2 304 575 and GB 2 304 708 generally describe methods which aim to meet these needs. It is also known from the former publication that a pesticide may be combined with a plant growth regulator to treat banana and plantain trees. Nonetheless, it remains a non-trivial problem in agronomy to apply the correct amount of a plant growth regulator at the correct time in the life cycle of a banana or plantain plant. The present invention provides a general method which offers improvements on the state of the art.

Sometimes it is necessary to arrest the growth of the mother plant when it is judged that the mother plant will not produce a commercially acceptable bunch of fruit. It is also desirable to arrest the growth of the mother plant in order to schedule the harvest of the subsequent daughter plant.

One way to arrest the growth of the mother plant is to cut the pseudotrunk and allow the daughter to grow. This method is commonly called in Spanish "vampiero", which in English means "suckering". When the mother plant is cut, the daughter plant "sucks" or absorbs nutrients from the mother plant and the mother plant dies back to the corm.

It is known that such suckering may be accomplished by the injection of ethephon (chloroethylphosphonic acid) into the mother plant. Such an injection causes loss of apical dominance in the mother plant and allows the mother to die gradually back to the corm. However, an undesired drawback to this type of chemical suckering is that the daughter plant often develops very undesirable foliage, known as "cabbaging". This is to say that the daughter plant foliage is highly bunched and generally cannot develop properly to produce acceptable fruit.

SUMMARY AND OBJECTS OF THE INVENTION

An object of the present invention is to provide new chemical compositions useful for the production of bananas and plantains.

Another object of the present invention is to provide an improved method of treating banana and plantain trees with pesticides.

Another object of the present invention is to provide a method of treatment of banana and plantain trees which is safe for the trees.

Another object of the present invention is to provide a method of treatment of banana and plantain trees which provides more production of the fruit per acre per year.

Another object of the present invention is therefore to increase the fruit yields of banana and plantain plantations.

Another object of the present invention is to increase the fruit yields of banana plantations, independently of the diseases by which these banana plants may be attacked or by which it may be supposed that they will be attacked.

Another object of the present invention is to increase the average weight per plant of the bunches of bananas produced by a banana plantation, independently of the diseases by which these banana plants may be attacked or by which it may be supposed that they will be attacked.

These objects may be met in whole or in part by the present invention.

The present invention provides a composition for use in cropping trees of the family Musaceae or Plantaginaceae which comprises a pesticide and a plant growth regulator, the composition being adapted for introduction into the pseudostem of the tree. Preferably the pesticide is an insecticide, nematicide or fungicide.

By the phrase "adapted for introduction into the pseudostem of the tree" is meant a composition which may be injected, added into a cavity, or may otherwise be partially or entirely inserted into the pseudostem. The pseudostem may also be called the pseudotrunk.

The present invention provides a method for the protection of two or more trees of the families Musaceae or Plantaginaceae from destructive pests wherein the trees to be protected share a common root system, which method comprises:

(a) cutting one of the trees sharing the said root system to remove its fruit; and (b) then introducing into the cut tree a pesticidal combination comprising at least one pesticidal component and a growth-accelerating amount of a plant growth regulator.

DETAILED DESCRIPTION OF THE INVENTION

In general, the plant growth regulator is an ethylene release agent, preferably a chemical compound that when chemically changed in the plant, releases ethylene ($CH_2CH_2$). A compound that is preferably used in the invention is chloroethylphosphonic acid, better known as ethephon, which is described in *The Pesticide Manual*, vide infra.

The growth-accelerating amount of the ethylene release agent is dependent on the agent itself. In the case of ethephon, the amount is from about 15 mg per tree to about 30 mg per tree, preferably from about 15 mg to about 25 mg, most preferably from about 18 mg to about 23 mg per tree.

The weight/weight ratio of the pesticide to the ethylene release agent is generally from about 40:1 to about 300:1, preferably from about 50:1 to about 200:1.

The pesticidal component is generally an insecticide, nematicide or fungicide. The pesticide is generally translocatable and more preferably water-soluble at ambient temperature, the water solubility being generally higher than about 0.5 g/l, preferably higher than about 2 g/l at ambient temperature. The pesticide can be provided in a formulation that is generally translocatable and more preferably water soluble at ambient temperature.

Those species of banana or plantain trees to be preferably protected according to the present invention are *Musa textilis, Musa sapientum,* or *Musa paradisica*.

The pesticide is generally introduced into the tree from zero to about thirty days after one of the trees is cut, preferably from about one to about seven days and even more preferably from about one to about three days.

A preferred group of insecticides or nematicides according to the invention comprises carbamates. Carbamates are a well-known group of pesticides; those skilled in the art will recognize these in *The Pesticide Manual,* 10th ed., edited by C. Tomlin, British Crop Protection Council, United Kingdom, 1994. A preferred group of carbamates are N-methyl carbamates, that is, those substances that possess the substituent —OC(O)NHMe. A particularly preferred carbamate that can be used according the instant invention is 2-methyl-2-(methylthio)propionaldehyde O-methylcarbamoyloxime (aldicarb). Other carbamates that can be used according to the invention are 2,3-dihydro-2,2-dimethylbenzofuran-7-yl methylcarbamate (carbofuran) and N,N-dimethyl-2-methylcarbamoyloxyimino-2-(methylthio) acetamide (oxamyl). A carbamate can be used alone or in combination with other pesticides.

Other insecticides or nematicides that can be used according to the instant invention either alone or in combination with other pesticides include:

nitromethylenes or nitroimines including 1-(6-chloro-3-pyridylmethyl)-N-nitroimidazolidin-2-ylideneamine (imidacloprid), thiacloprid, or thiamethoxam; and cyanoimines; and organophosphates including S,S-di-sec-butyl O-ethyl phosphorodithioate (cadusafos); (RS)-S-sec-butyl O-ethyl 2-oxo-1,3-thiazolidin-3-ylphosphonothioate (fosthiazate); and O-ethyl S,S-dipropyl phosphorodithioate (ethoprophos).

Other insecticides or nematicides that can be used according to the instant invention either alone or in combination with other pesticides include compounds of formula (I):

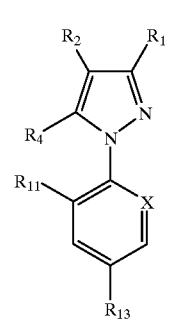

in which:

$R_1$ is —CN or methyl;

$R_2$ is —S(O)$_n$R$_3$;

$R_3$ is alkyl or haloalkyl;

$R_4$ represents a hydrogen or halogen atom or a member of the group consisting of —NR$_5$R$_6$, —S(O)$_m$R$_7$, —C(O)O—R$_7$, alkyl, haloalkyl, —OR$_8$ and —N=C(R$_9$)(R$_{10}$);

$R_5$ and $R_6$ independently represent the hydrogen atom or an alkyl, haloalkyl, —C(O)alkyl, alkoxycarbonyl or —S(O)$_r$CF$_3$ radical; or $R_5$ and $R_6$ can together form a divalent alkylene radical which can be interrupted by one or two divalent heteroatoms, such as oxygen or sulfur;

$R_7$ represents an alkyl or haloalkyl radical;

$R_8$ represents an alkyl or haloalkyl radical or a hydrogen atom;

$R_9$ represents an alkyl radical or hydrogen atom;

$R_{10}$ represents a phenyl or heteroaryl group which is unsubstituted or substituted by one or more halogen atoms or a member of the group consisting of —OH, —O-alkyl, —S-alkyl, cyano, and alkyl;

X represents a trivalent nitrogen atom or a C—R$_{12}$ radical, the other three valences of the carbon atom forming part of the aromatic ring;

$R_{11}$ and $R_{12}$ represent, independently of each other, a hydrogen or halogen atom;

$R_{13}$ represents a halogen atom or a haloalkyl, haloalkoxy, —S(O)$_q$CF$_3$ or SF$_5$ group; and m, n, q, and r represent, independently of one another, an integer equal to 0, 1, or 2;

provided that, when $R_1$ is methyl, then $R_3$ is haloalkyl, $R_4$ is —NH$_2$, $R_{11}$ is —Cl, $R_{13}$ is CF$_3$ and X is N.

Alkyl groups and moieties in formula (I) are generally of 1 to 6 carbon atoms and are straight- or branched-chain. The ring formed by $R_5$ and $R_6$ with the nitrogen atom to which they are attached when they represent a divalent alkylene group is generally a 5-, 6- or 7-membered ring.

A preferred group of compounds of formula (I) is one in which:

$R_1$ is CN;

$R_3$ is a haloalkyl radical;

$R_4$ is $NH_2$;

X is C—$R_{12}$;

$R_{11}$ and $R_{12}$ represent, independently of each other, a halogen atom; and $R_{13}$ is a haloalkyl radical.

A preferred compound of formula (I) is 5-amino-1-(2,6-dichloro-4-trifluoromethylphenyl)-4-trifluoromethylsulfinyl-3-cyanopyrazole.

Compounds of formula (I) may be prepared according to known processes, for example, as described in International Patent Publications No. WO 87/03781, 93/06089 and 94/21606 as well as in European Patent Publications Nos. 0295117, 0403300, 0385809 and 0679650, German Patent Publication No. 19511269 and U.S. Pat. Nos. 5,232,940 and 5,236,938, or other process according to the knowledge of a man skilled in the art of chemical synthesis.

Fungicides that may be used according to the instant invention include:

methyl 1-(butylcarbamoyl)benzimidazol-2-ylcarbamate (benomyl);

triazoles, including (±)-1-[2-(2,4-dichlorophenyl)-4-propyl-1,3-dioxolan-2-ylmethyl]-1H-1,2,4-triazole (propiconazole); and 1-[(2RS,4RS:2RS,4SR)-4-bromo-2-(2,4-dichlorophenyl)tetrahydrofurfuryl]-1H-1,2,4-triazole (bromuconazole); or a metal salt of a mono-alkyl phosphonate wherein the metal cation is mono-, di- or trivalent, phosphorous acid, or a phosphorous acid salt.

Generally, the mono-alkyl phosphonate contains from 2 to 4 carbon atoms, preferably 2. The metal cation of the mono-alkyl phosphonate is generally selected from groups 1a, 2a and 3a of the periodic table as found on page B-4 of *The Handbook of Chemistry and Physics,* 56$^{th}$ edition, 1975, CRC Press. Most preferably, the metal cation of the mono-alkyl phosphate is the aluminum cation.

Generally, the salt of phosphorous acid contains a metal cation preferably chosen from groups 1a, 2a or 3a of the periodic table vide supra. Most preferably, the pesticide is the aluminum salt of ethyl hydrogen phosphonate, also known as fosetyl-aluminum as described in *The Pesticide Manual,* 11th edition, Clive Tomlin, editor, British Crop Protection Council, 1997, pp. 629–630.

According to a preferred method of the invention, the banana plants on which the pesticidal composition is applied are healthy banana plants. "Healthy banana plants" is understood to mean banana plants exhibiting no symptom characteristic of diseases or parasites known to affect them, such as, but not exclusively, Fusarium disease or Cercospora disease. The healthy banana plants can in particular be banana plants forming the subject of a conventional preventive treatment against fungal diseases, said treatment being known to have no effect on the fruit yield.

According to another aspect of the invention, a dose, e.g., an additional dose, of the pesticidal combination is introduced into the pseudostem of a tree of the family Musaceae or Plantaginaceae which is at or just before the flowering stage, the pesticidal composition having at least one pesticidal component and a plant growth regulator.

The pesticidal combination is preferably introduced into the pseudostem at a time from 30 days before flowering until 10 days after flowering, preferably from 20 days before flowering to 5 days after flowering.

Preferably, the pesticidal component is a metal salt of a mono-alkyl phosphonate wherein the metal cation is mono-, di- or trivalent or phosphorous acid or a phosphorous acid salt.

When the pesticidal component is a metal salt of a mono-alkyl phosphonate wherein the metal cation is mono-, di- or trivalent or phosphorous acid or a phosphorous acid salt, the dose of the active ingredient is generally from about 1 to about 12.5 g of the active ingredient per plant, preferably from about 2 to about 7.5 g per plant, most preferably from about 2 to about 3 grams. The amount of the plant growth regulator is quite specific to the regulator itself, but in the case of ethephon, the amount is from about 1 mg to about 14 mg per tree, preferably from about 1 to about 10 mg per tree, more preferably from about 2 to about 8 mg per tree, most preferably from about 3 to about 7 mg per tree.

In this aspect of the invention, the combination of the pesticidal component and the plant growth regulator generally is provided in a weight/weight ratio of the pesticidal component to plant growth regulator of from about 10:1 to about 1000:1, preferably from about 100:1 to about 600:1.

The combination is generally applied as a composition which can additionally comprise all the usual additives or adjuvants of plant-protection compositions, especially surface-active agents, adhesion agents and flow-improving agents.

In the present account, the term "vehicle" denotes a natural or synthetic, organic or inorganic material with which the active materials are combined to facilitate their application on the plant. This vehicle is thus generally inert and it must be acceptable in agriculture, especially on the treated plant. The vehicle can be solid (e.g., clays, natural or synthetic silicates, silica, resins, waxes, or solid fertilizers) or liquid (e.g., water, alcohols, ketones, petroleum fractions, aromatic or paraffinic hydrocarbons, chlorinated hydrocarbons, or liquefied gases).

The surface-active agent can be an emulsifying, dispersing or wetting agent of ionic or nonionic type. There may be mentioned, for example, salts of polyacrylic acids, salts of lignosulfonic acids, salts of phenolsulfonic or naphthalenesulfonic acids, polycondensates of ethylene oxide with fatty alcohols or with fatty acids or with fatty amines, substituted phenols (especially alkylphenols or arylphenols), salts of esters of sulfosuccinic acids, taurine derivatives (especially alkyltaurates) or phosphoric esters of polyoxyethylenated phenols or alcohols. The presence of at least one surface-active agent is desirable to promote dispersion of the active materials in water and their ready application to the plants.

This composition can also contain any kind of other compatible ingredients such as, for example, protective colloids, adhesives, thickening agents, thixotropic agents, penetrating agents, stabilizing agents, sequestering agents, pigments, dyes or polymers.

More generally, the composition which can be used in the process according to the invention and/or subject of the invention can include any of the solid or liquid additives corresponding to the usual techniques for the formulation of plant-protection products.

This composition can be in the solid, gel or liquid form and, in the latter case, in the form of solutions or suspensions. Liquid compositions are preferred, due both to their convenience of use and to their simplicity of manufacture.

There may be mentioned, as forms of solid compositions, powders for dusting or dispersion (with an active compounds content which can range up to 100%), wettable powders and dispersible or soluble granules.

Wettable powders (or powders to be sprayed), as well as dispersible granules, generally contain from about 20 to about 95% of active materials and, in addition to the solid vehicle, from 0 to about 5% of a wetting agent, from about 3 to about 10% of a dispersing agent and, when necessary, from 0 to about 10% of one or more stabilizing agents and/or other additives, such as pigments, dyes, penetrating agents, adhesives, or anticlumping agents. It is well understood that some of these compositions, such as wettable powders or dispersible granules, are intended to constitute liquid compositions at the time of application.

There may be mentioned, as forms of liquid compositions, solutions, in particular water-soluble concentrates, suspension concentrates or pastes.

The soluble concentrates most often comprise from about 10 to about 80% of active material, the solutions ready for application containing, for their part, from about 0.01 to about 20% of active material. As has already been said, aqueous dispersions, for example, the compositions obtained by diluting a wettable powder according to the invention with water, come within the general scope of the present invention.

The suspension concentrate, also applicable by spraying, is a stable fluid product, which does not thicken or form a sediment after storage, and it generally contains from about 10 to about 75% of active materials, from about 0.5 to about 15% of surface-active agents, from about 0.1 to about 10% of thixotropic agents and from 0 to about 10% of suitable additives, such as pigments, dyes, antifoaming agents, corrosion inhibitors, stabilizing agents, penetrating agents and adhesives and, as vehicle, water or an organic liquid in which the active materials are insoluble or nearly insoluble. Certain organic solid materials or inorganic salts can be dissolved in the vehicle to aid in preventing sedimentation or as antigels for water.

The compositions described above may be prepared according to processes known per se.

Thus, to obtain powders to be sprayed or wettable powders, the active materials are intimately mixed, in suitable mixers, with the additional substances, and the mixture is milled with mills or other grinders. Powders to be sprayed are thereby obtained with advantageous wettability and suspensibility; they can be suspended in water at any desired concentration and these suspensions can be used very advantageously.

Pastes or suspension concentrates can be produced in place of wettable powders. The conditions and modes of production and use of these pastes are similar to those of wettable powders or powders to be sprayed, part of the milling operation necessary simply being carried out in a liquid medium.

The dispersible granules are generally prepared by agglomeration or extrusion or compacting, in suitable granulation systems, of compositions of wettable powder type.

The present invention also provides a product comprising a pesticidal component and a plant growth regulator for simultaneous, separate or sequential use in controlling the growth of bananas or plantains.

The present invention also provides a method of chemical suckering of a tree of the family Musaceae or Plantaginaceae which comprises introducing into the mother tree an amount of a combination effective to arrest apical dominance in the mother tree comprising:

(i) a pesticide, which pesticide is preferably a first component which is selected from the group consisting of a metal salt of a mono-alkyl phosphonate wherein the metal cation is mono-, di- or trivalent; phosphorous acid; and a phosphorous acid salt; and (ii) a plant growth regulator, preferably an ethylene release agent.

Generally the mono-alkyl phosphonate contains from 2 to 4 carbon atoms, preferably 2. The metal cation of the mono-alkyl phosphonate is generally selected from groups 1a, 2a and 3a of the periodic table as found on page B-4 of *The Handbook of Chemistry and Physics*, $56^{th}$ edition, 1975, CRC Press. Most preferably, the metal cation of the mono-alkyl phosphate is the aluminum cation.

Generally, the salt of phosphorous acid contains a metal cation preferably chosen from groups 1a, 2a or 3a of the periodic table vide supra. Most preferably, the first component is the aluminum salt of ethyl hydrogen phosphonate, also known as fosetyl-aluminum as described in *The Pesticide Manual*, $11^{th}$ edition, Clive Tomlin, editor, British Crop Protection Council, 1997, pp. 629–630.

The salts of the mono alkyl phosphonate and phosphorous acid are generally agriculturally acceptable.

Generally, the ethylene release agent is a chemical compound that when chemically changed in the plant, releases ethylene ($CH_2CH_2$). A compound that is preferably used in the invention is chloroethylphosphonic acid, better known as ethephon, which is described in *The Pesticide Manual*, pp. 477–478, vide supra.

In general, *The Pesticide Manual* provides commercial sources of the active ingredients. Fosetyl-Al is generally available and conveniently used as Aliette® 80WG and ethephon as Ethrel®, both available from Rhone-Poulenc Agro, S.A.

Measured on a basis of a dose per mother tree, the combination or composition for use in the method of suckering generally contains from about 1 to about 10 grams, preferably from about 2 to about 8 grams, more preferably from about 2 to about 6 grams of the first component, most preferably from about 2 to about 3 grams, in the case of fosetyl-aluminum.

Measured on a basis of a dose per mother tree, the combination or composition for use in the method of suckering generally contains from about 31 to about 100 mg, preferably from about 31 to about 70 mg, most preferably from about 35 to 50 mg of the ethylene release agent. In the case of ethephon, it is most preferable to use from about 40 to about 45 mg of ethephon.

The composition is generally aqueous. Measured on a basis of a dose per mother tree, the composition generally contains from about 5 to about 50 mL of water, preferably from about 10 to about 40 mL, most preferably from about 15 to about 25 mL.

Generally, the combination or composition for use in the method of suckering comprises a weight/weight ratio of the first component to the ethylene release agent of from about 10:1 to about 500:1, preferably from about 10:1 or 20:1 to about 350:1 or 400:1, more preferably from about 40:1 to about 300:1, even more preferably from about 50:1 to about 200:1, and most preferably from about 60:1 to about 100:1.

Generally, the combination or composition for use in the method of suckering comprises a weight/weight ratio of the ethylene release agent to water of from about 1:2500 to about 1:50, preferably from about 1:2000 to about 1:100, more preferably from about 1:1500 to about 1:200, even more preferably from about 1:1000 to about 1:300, even more preferably from about 1:750 to about 1:350, and most preferably from about 1:600 to about 1:400.

Generally, the combination or composition for use in the method of suckering comprises a weight/weight ratio of the first component to water of from about 1:50 to about 2:1, preferably from about 1:25 to about 1:1, more preferably from about 1:20 to about 1:3 or 4, most preferably from about 1:10 to about 1:5.

The composition for use in the method of suckering may further comprise another agrochemical. The additional agrochemical may be an insecticide, a nematicide, a fungicide, or another plant growth regulator. If the additional agrochemical is a plant growth regulator, it is preferably a cytokinin or a gibberellin such as gibberellic acid.

A preferred group of insecticides or nematicides that may be used according to the invention are carbamates. Those skilled in the art will find these in *The Pesticide Manual*, vide supra. A preferred group of carbamates are N-methyl carbamates, that is, those substances that possess the substituent —OC(O)NHMe. A particularly preferred carbamate that can be used according to the instant invention is 2-methyl-2-(methylthio)propionaldehyde-O-methylcarbamoyloxime (aldicarb). Other carbamates that can be used according to the invention are 2,3-dihydro-2,2-dimethylbenzofuran-7-yl methylcarbamate (carbofuran) and N,N-dimethyl-2-methylcarbamoyloxyimino-2-(methylthio) acetamide (oxamyl). A carbamate can be used alone or in combination with other pesticides.

Other insecticides or nematicides that can be used according to the instant invention either alone or in combination with other pesticides include:

nitromethylenes or nitroimines, including 1-(6-chloro-3-pyridylmethyl)-N-nitroimidazolidin-2-ylideneamine (imidacloprid);

cyanoimines, including (E)-N$^1$-[(6-chloro-3-pyridyl)methyl]-N$^2$-cyano-N$^1$-methylacetamidine (acetamiprid); and organophosphates, including S,S-di-sec-butyl O-ethyl phosphorodithioate (cadusafos); (RS)-S-sec-butyl O-ethyl 2-oxo-1,3-thiazolidin-3-ylphosphonothioate (fosthiazate); and O-ethyl S,S-dipropyl phosphorodithioate (ethoprophos).

Other insecticides or nematicides that can be used according to the instant invention, either alone or in combination with other pesticides, include compounds of formula (I):

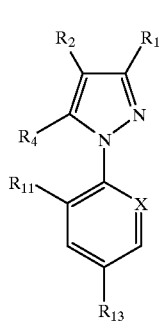

(I)

in which:
R$_1$ is CN or methyl or a halogen atom;
R$_2$ is —S(O)$_n$R$_3$ or 4,5-dicyanoimidazol-2-yl or haloalkyl;
R$_3$ is alkyl or haloalkyl;
R$_4$ is selected from hydrogen, halogen, —NR$_5$R$_6$, —C(O)OR$_7$, —S(O)$_m$R$_7$, alkyl, haloalkyl, —OR$_8$ and —N=C(R$_9$)(R$_{10}$) and C(O)alkyl;
R$_5$ and R$_6$ are independently selected from a hydrogen atom, alkyl, haloalkyl, —C(O)alkyl, —C(O)OR$_7$, and —S(O)$_r$CF$_3$; or R$_5$ and R$_6$ together form a divalent alkylene radical which can be interrupted by one or two divalent heteroatoms, such as oxygen or sulfur;
R$_7$ is alkyl or haloalkyl;
R$_8$ is alkyl, haloalkyl or hydrogen;
R$_9$ is alkyl or hydrogen;
R$_{10}$ is selected from phenyl and heteroaryl, each of which is unsubstituted or substituted by one or more halogen, hydroxy, —O-alkyl, —S-alkyl, cyano, or alkyl;
X is selected from nitrogen and C—R$_{12}$;
R$_{11}$ and R$_{12}$ are independently selected from halogen, hydrogen, CN and NO$_2$;
R$_{13}$ is selected from halogen, haloalkyl, haloalkoxy, —S(O)$_q$CF$_3$ and —SF$_5$;
m, n, q, and r are independently selected from 0, 1, and 2;
provided that, when R$_1$ is methyl, then R$_3$ is haloalkyl, R$_4$ is NH$_2$, R$_{11}$ is Cl, R$_{13}$ is CF$_3$ and X is N, and provided that, when R$_2$ is 4,5-dicyanoimidazol-2-yl, R$_4$ is Cl, R$_{11}$ is Cl, R$_{13}$ is CF$_3$ and X is =C—Cl.

The alkyl and alkoxy groups and moieties of the formula (I) are preferably lower alkyl and alkoxy groups, that is, groups having one to six carbon atoms. The haloalkyl and haloalkoxy groups likewise preferably have one to four carbon atoms. The haloalkyl and haloalkoxy groups can bear one or more halogen atoms; preferred groups of this type include —CF$_3$ and —OCF$_3$. It shall be understood that the ring formed by the divalent alkylene radical represented by R$_5$ and R$_6$ and including the nitrogen atom to which R$_5$ and R$_6$ are attached is generally a 5, 6, or 7-membered ring. When R$_{10}$ is heteroaryl, it is preferably pyridyl, most preferably 2-pyridyl. It will be understood that the 1-arylpyrazoles of formula (I) include enantiomers and/or diastereomers thereof.

A preferred group of 1-arylpyrazoles for use in the present invention are those of formula (I) with one or more of the following features:
R$_1$ is CN;
R$_4$ is —NR$_5$R$_6$;
R$_5$ and R$_6$ are independently selected from the hydrogen atom, alkyl, haloalkyl, C(O)alkyl, and C(O)OR$_7$;
X is C—R$_{12}$; or
R$_{13}$ is selected from a halogen atom, haloalkyl, haloalkoxy, and —SF$_5$.

Another preferred group of 1-arylpyrazoles of formula (I) for use in the present invention is that wherein:
R$_1$ is CN;
R$_3$ is a haloalkyl radical;
R$_4$ is NH$_2$;
X is C—R$_{12}$;
R$_{11}$ and R$_{12}$ represent, independently of each other, a halogen atom; and
R$_{13}$ is a haloalkyl radical.

A most preferred compound is 5-amino-1-(2,6-dichloro-4-trifluoromethylphenyl)-4-trifluoromethylsulfinyl-3-cyanopyrazole.

Compounds of formula (I) may be prepared according to known processes, for example as described in International Patent Publications No. WO 87/03781, 93/06089 and 94/21606 as well as in European Patent Publications 0295117, 0403300, 0385809 and 0679650, German Patent Publication No. 19511269 and U.S. Pat. Nos. 5,232,940 and 5,236,938, or other process according to the knowledge of a man skilled in the art of chemical synthesis.

Fungicides that may be used according to the instant invention include:

methyl 1-(butylcarbamoyl)benzimidazol-2-ylcarbamate (benomyl);

triazoles, including (±)-1-[2-(2,4-dichlorophenyl)-4-propyl-1,3-dioxolan-2-ylmethyl]-1H-1,2,4-triazole (propiconazole); and 1-[(2RS,4RS:2RS,4SR)-4-bromo-2-(2,4-dichlorophenyl)
tetrahydrofurfuryl]-1H-1,2,4-triazole
(bromuconazole).

The composition of the invention may also comprise other known ingredients known to the skilled addressee for formulation of agrochemicals into an agrochemically acceptable composition. Such ingredients may be found, for example, in the patent publications herein described.

The formulation is generally liquid, but may also be a particulate solid or in the form of a shaped article, such as a tablet.

The composition is generally administered to the mother tree when the mother tree is greater than about one meter in height, preferably greater than about 1.5 meters in height. The composition is generally administered to the pseudotrunk of the mother plant by injection of a liquid formulation or via a sachet comprising a liquid or solid placed in a hole in the pseudotrunk or as a shaped article pushed into the pseudotrunk. Generally, the composition is administered to the mother tree at a height of from about 20 to about 100 cm from the ground, preferably from about 30 to about 50 cm from the ground.

The invention also provides a product which comprises the first component and the ethylene release agent for simultaneous, separate or sequential use in chemical suckering.

The following examples are given purely by way of illustration and without implied limitation of the advantageous properties of the process and of the composition according to the invention. In the examples using fosetyl-Al and ethephon, these are generally applied as Aliette® 80WG and Ethrel®, respectively.

EXAMPLE 1

In vivo test of the application of a composition comprising fosetyl-Al and ethephon by injection into the growing pseudostem:

The test is carried out on a plantation of banana plants which have reached a stage of regular fruit production. This plantation is furthermore treated periodically throughout the duration of the test by means of a conventional preventive treatment against various fungal diseases, as well as against harmful insects and nematodes, which treatment is known to have no effect of the type of those observed below with fosetyl-Al.

An aqueous composition comprising fosetyl-Al and ethephon is injected into the pseudostem of the growing banana plants, in the proportion of 6 kg/ha (i.e. about 2.6 g of fosetyl-Al per plant and about 5 mg of ethephon), 1 month before flowering.

The fruits are harvested 4 months later. The harvest of the bananas from the trees treated with the pesticidal composition are harvested sooner than with fosetyl-Al alone, thus increasing the productivity of the plantation.

EXAMPLE 2

Banana trees are grown in a plantation. The trees are disposed as mother plants having a series (1 to 5) of daughter plants growing from the corm. Just before harvesting the mother plants, the daughter plants are removed except one daughter plant per mother plant.

The fruit of the banana trees are harvested by cutting the sets of fruits. Within one week after this harvest, the pseudo of these plants are cut to remove the canopies. After two days, a wedge is cut from the surface resulting from the removal of the canopy of each pseudotrunk of each mother tree. A dose of about 2.6 grams of fosetyl-Al and 20 mg of ethephon in the form of a sachet granular formulation is placed in the empty space from which each wedge was removed and the wedges are replaced.

The daughter plants are protected against both nematodes and weevils up to harvest time of the daughter trees which is 35 weeks later, thus providing economically acceptable fruit. The risk of worker exposure is greatly reduced. The nematode protection is better with the applied composition than with fosetyl-Al alone.

EXAMPLE 3

Banana trees are grown in a plantation. The trees are disposed as mother plants having a series (1 to 5) of daughter plants growing from the corm. Just before harvesting the mother plants, the daughter plants are removed except one daughter plant per mother plant.

The fruit of the banana trees are harvested by cutting the sets of fruits. Within one week after this harvest, the pseudo of these plants are cut to remove the canopies. After two days, a wedge is cut from the surface resulting from the removal of the canopy of each pseudotrunk of each mother tree. A dose of 0.5 g per tree of 2-methyl-2-(methylthio) propionaldehyde O-methylcarbamoyloxime and 20 mg ethephon in the form of a 15% w/w granular formulation is placed in the empty space from which each wedge was removed and the wedges are replaced.

The daughter plants are protected against both nematodes and weevils up to harvest time of the daughter trees which is 35 weeks later, thus providing economically acceptable fruit. The risk of worker exposure is greatly reduced. The control of nematodes is better than with 2-methyl-2-(methylthio)propionaidehyde O-methylcarbamoyloxime used alone.

In all the above examples, in general, the bunch weights (that is, yields per hectare) are increased, the root weights are increased, time for ratooning is decreased (thus providing the farmer better productivity per acre), fruit hanging time is decreased, and nematode populations are decreased. The overall economic advantages to the grower are substantial.

EXAMPLE 4

The experiments were carried out on a banana plantation wherein there were placed mother plants with one daughter plant per mother. In a first plot, 100 mother banana plants were treated with a composition comprising 2.6 g of fosetyl-aluminum and 45 mg of chloroethylphosphonic acid in the forms of Aliette® and Ethrel®, respectively. In a second plot, 100 mother banana plants were treated with 45 mg of chloroethylphosphonic acid in the form of Ethrel®. The following observations were made:

A) After 7 to 21 days after treatment, all the mother plants lost apical dominance and began to die.

B) At 70 days after treatment, the average height and circumference of the daughter plants in the first plot was greater than those of the second plot.

C) At 70 and 160 days after treatment, the average circumference of the daughter plants in the first plot was greater than those of the second plot.

D) The daughter plants flowered earlier in the first plot than in the second plot.

E) The daughter plants in the first plot had a greater percentage of functional roots than those in the second plot.

F) The fruit that developed on the daughter plants was harvested on average 21 days earlier in the first plot than in the second plot.

G) There was 7% more fruit harvested from the first plot than the second plot.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A method of chemical suckering a tree of the family Musaceae or Plantanginaceae, which comprises introducing into a mother tree of the family Musaceae or Plantanginaceae an amount of a pesticidal composition effective to arrest apical dominance in the mother tree, said pesticidal composition comprising:
   (i) a pesticide which is fosetyl-Al; and
   (ii) a plant growth regulator.

2. A method according to claim 1, wherein the plant growth regulator is an ethylene release agent.

3. A method according to claim 2, wherein the ethylene release agent is ethephon.

4. A method according to claim 1, wherein the weight/weight ratio of the pesticide to the plant growth regulator is from about 10:1 to about 350:1.

5. A method according to claim 1, wherein the amount of the plant growth regulator, based on a dose per mother tree, ranges from about 31 mg to 100 mg.

6. A method according to claim 1, wherein the amount of the pesticide, based on a dose per mother tree, ranges from about 1 mg to 10 mg.

7. A method according to claim 1, wherein the pesticidal composition contains, based on the dose to the mother tree,
   from 1 to 10 grams of fosetyl-Al; and
   from 31 to 100 mg of ethephon.

8. A method for protecting two or more trees from destructive pests, wherein the trees to be protected are of the families Musaceae or Plantanginaceae, and share a common root system, said method comprises:
   (a) cutting at least one of the trees sharing said root system to remove its fruit;
   (b) introducing into said cut tree a pesticidal composition comprising at least one pesticidal component and a growth-accelerating amount of a plant growth regulator, and
   (c) introducing an additional dose of said pesticidal composition into the pseudostem of at least one uncut tree.

9. A method according to claim 8, wherein the additional dose of the pesticidal composition is introduced into a daughter tree.

10. A method according to claim 8, wherein the additional dose of the pesticidal composition is introduced at the flowering stage.

11. A method according to claim 8, wherein the amount of the plant growth regulator, based on a dose per tree to be protected, ranges from about 15 mg to 30 mg.

12. A method according to claim 8, wherein the amount of the plant growth regulator, based on said additional dose per tree, ranges from about 1 mg to 14 mg.

13. A method according to claim 8, wherein the plant growth regulator is ethephon.

14. A method according to claim 8, wherein the at least one pesticidal component is fosetyl-Al.

15. A method according to claim 8, wherein said composition contains, based on dose per cut tree,
   from 1 to 10 grams of fosetyl-Al; and
   from 31 to 100 mg of ethephon.

16. A method according to claim 8, wherein said composition contains, based on the additional dose per tree,
   from 1 to 12.5 grams of fosetyl-Al; and
   from 1 to 14 mg of ethephon.

17. A method for protecting two or more trees from destructive pests, wherein the trees to be protected are of the families Musaceae or Plantanginaceae and share a common root system, said method comprising:
   (a) cutting at least one of the trees sharing said root system to remove its fruit; and
   (b) introducing into said cut tree a pesticidal composition comprising at least one pesticidal component which is fosetyl-Al, and a growth-accelerating amount of a plant growth regulator.

18. A method according to claim 17, wherein the plant growth regulator is ethephon.

19. A method according to claim 17, wherein the weight/weight ratio of the pesticide to the plant growth regulator ranges from 40:1 to 300:1.

20. A method according to claim 17, wherein the amount of the plant growth regulator, based on the dose per tree, ranges from about 15 mg to 30 mg.

21. A method according to claim 17, wherein the pesticidal composition contains, based on the dose per cut tree,
   from 1 to 10 grams of fosetyl-Al; and
   from 31 to 100 mg of ethephon.

* * * * *